US007349729B2

(12) United States Patent
Reeder et al.

(10) Patent No.: US 7,349,729 B2
(45) Date of Patent: Mar. 25, 2008

(54) MAGNETIC RESONANCE IMAGING OF DIFFERENT CHEMICAL SPECIES IN A SYSTEM HAVING MAGNETIC FIELD HETEROGENEITIES

(75) Inventors: Scott B. Reeder, Menlo Park, CA (US); Norbert J. Pelc, Los Altos, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 633 days.

(21) Appl. No.: 10/690,230

(22) Filed: Oct. 20, 2003

(65) Prior Publication Data

US 2005/0085713 A1 Apr. 21, 2005

(51) Int. Cl.
*A61B 5/05* (2006.01)

(52) U.S. Cl. ...................................... 600/410; 600/407

(58) Field of Classification Search ..................... None
See application file for complete search history.

(56) References Cited

U.S. PATENT DOCUMENTS

| | | | | |
|---|---|---|---|---|
| 5,225,781 A * | 7/1993 | Glover et al. | ............... | 324/309 |
| 6,091,243 A * | 7/2000 | Xiang et al. | ................ | 324/307 |
| 6,856,134 B1 | 2/2005 | Reeder et al. | | |

OTHER PUBLICATIONS

Reeder et al., "Rapid MR Imaging of Articular Cartilage with Steady-State Free Precession and Multipoint Fat-Water Separation," 2003, *American Journal of Radiology*, vol. 180, pp. 357-362.

Reeder et al., "Rapid Cartilage Imaging with SSFP and Four-Point Dixon Techniques", 2002, *ISMRM*, Poster/Abstract.

Dixon, "Simple Proton Spectroscopic Imaging", 1984, *Radiology*, vol. 153, pp. 189-194.

Glover, "Multipoint Dixon Technique for Water and Fat Proton and Susceptibility Imaging", 1991, *Journal of Magnetic Resonance Imaging* , vol. 1, pp. 521-530.

Rybicki et al., "Fast Three-Point Dixon MR Imaging Using Low-Resolution Images for Phase Correction: A Comparison with Chemical Shift Selective Fat Suppression for Pediatric Musculoskeletal Imaging", 2001, *American Journal of Radiology*, vol. 177, pp. 1019-1023.

Bredella et al., "Three-Point Dixon Chemical-Shift Imaging for Evaluating Articular Cartilage Defects in the Knee Joint on a Low-Field-Strength Open Magnet", 2001, *American Journal of Radiology*, vol. 177, 1371-1375.

Xiang et al., "Water-Fat Imaging with Direct Phase Encoding", 1997, *Journal of Magnetic Resonance Imaging*, vol. 7, pp. 1002-1015.

* cited by examiner

*Primary Examiner*—Brian Casler
*Assistant Examiner*—James Kish
(74) *Attorney, Agent, or Firm*—Beyer Weaver LLP

(57) ABSTRACT

A multi-point chemical species (e.g., water, fat) separation process which is compatible with rapid gradient echo imaging such as SSFP uses an iterative least squares method that decomposes water and fat images from source images acquired at short echo time increments. The single coil algorithm extends to multi-coil reconstruction with minimal additional complexity.

17 Claims, 15 Drawing Sheets

OBTAIN M+1 MRI SIGNALS FOR M SPECIES AT M+1 ECHO TIMES, TE

↓

ESTIMATE SPECIES SIGNALS AT EACH PIXEL USING LEAST-SQUARES FITTING AND ASSUMED MAGNETIC FIELD MAP

↓

CALCULATE A FIRST ERROR TO ASSUMED FIELD MAP

↓

ESTIMATE SPECIES SIGNALS USING LEAST-SQUARES FITTING AND NEW FIELD MAP

↓

CALCULATE A SECOND ERROR TO FIELD MAP

↓

REPEAT STEPS 4 AND 5 UNTIL CALCULATED ERROR IS ACCEPTABLE

Fig. 2A
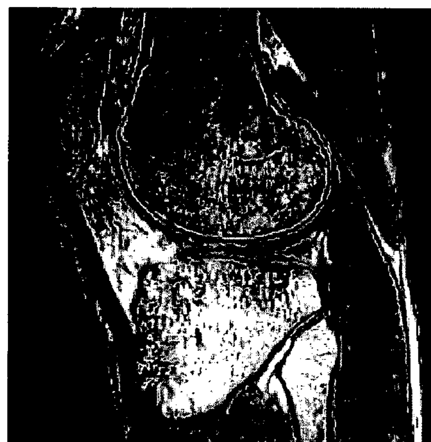
Fig. 2C
Fig. 2B
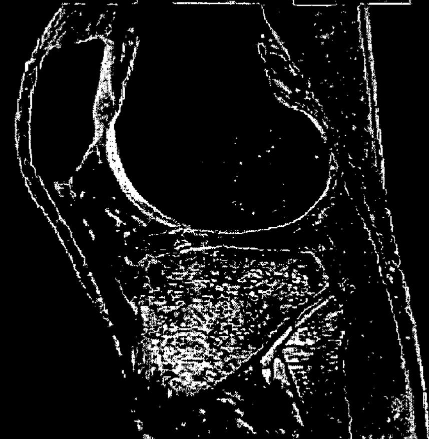
Fig. 2D

MAGNETIC RESONANCE IMAGING OF DIFFERENT CHEMICAL SPECIES IN A SYSTEM HAVING MAGNETIC FIELD HETEROGENEITIES

GOVERNMENT RIGHTS

The U.S. government has rights in the disclosed invention pursuant to NIH Grant No. P41RR09784 to Stanford University.

BACKGROUND OF THE INVENTION

This invention relates generally to magnetic resonance imaging of an object having different chemical species therein, such as fat and water, and more particularly the invention relates to species imaging in the presence of magnetic field heterogeneity.

The ability to image different chemical species such as fat and water using magnetic resonance techniques is particularly important in medical applications. For example, imaging and diagnosis of articular cartilage abnormalities has become increasingly important in the setting of an aging population where osteoarthritis is second only to cardiovascular disease as a cause of chronic disability. Accurate assessment of articular cartilage is also essential with the advent of surgical and pharmacological therapies that require advanced imaging techniques for initial diagnosis and management of disease progression.

Ideal imaging of articular cartilage requires high resolution and good contrast with adjacent tissues; this can be markedly improved with fat suppression techniques. In addition, bright appearance of synovial fluid is advantageous as it provides an arthroscopic effect and "fills in" defects in articular cartilage, increasing the conspicuity of cartilage irregularities. Separating fat and water can increase the conspicuity of the both the water (for most applications) and fat (for special applications) with many types of pulse sequences and with both T1 and T2 weighted sequences.

The difficulty in decomposing different chemical species is compounded by the presence of magnetic field heterogeneity. Separation of fat and water through "in-phase" and "out-of-phase" imaging is an approach first demonstrated by Dixon, Radiology 1984; 153: 189-194, and further refined by Glover, Journal of Magnetic Resonance Imaging 1991; 1:521-530, to compensate for the effects of magnetic field heterogeneities. In Glover's work, a three-point sampling scheme that acquires spin-echo or gradient echo images with echo time (TE) increments of 0, 2.2, and 4.4 ms, and produce phase increments of 0, $\pi$, and $2\pi$, when the frequency difference between fat and water is approximately −220 Hz at 1.5 T. The mathematics for this special case are greatly simplified and post-processing calculations are faster; however, these values of TE lengthen the minimum TR and would cause severe image degradation with SSFP imaging, for example, in the presence of typical magnetic field heterogeneities. Application of "Dixon" imaging to fast spin-echo (FSE) sequences has also been limited because the acquisition of echoes at different time shifts with respect to the spin-echo increases the spacing between successive refocusing pulses (echo spacing). Increasing the echo spacing reduces the number of echoes that can be collected in a time that maintains acceptable blurring from T2 decay, offsetting the scan time benefits of FSE. A fat-water separation method that permitted shorter time increments would reduce the time between refocusing pulses and be beneficial to fast spin-echo imaging.

SSFP is a rapid gradient echo imaging technique with renewed interest in recent years, owing to widespread availability of high speed gradient systems. SSFP has superior signal to noise ratio (SNR) compared to other gradient echo techniques and has excellent contrast behavior that has mixed dependence on T1 and T2. In particular, synovial fluid appears bright on SSFP images owing to its long T2. The major limitation of SSFP is severe image degradation caused by local magnetic field heterogeneities if the repetition time (TR) is long.

SUMMARY OF THE INVENTION

The present invention utilizes a multi-point chemical species separation process which is compatible with a rapid gradient echo imaging technique, such as SSFP, fast spin echo, echo planar imaging, spin echo, spiral imaging, and other similar pulse sequences. An iterative least squares fitting algorithm is utilized to combine signals at different echo times using an assumed initial value of field heterogeneity. A calculated value of field heterogeneity error is then obtained from the combined signals, and a new value of combined signals is obtained using the initially assumed value of field heterogeneity and the calculated error. An updated value of error in the field heterogeneity estimate is calculated and the process is repeated until an acceptable error value is realized.

The linear combination technique facilitates the estimation of water and fat images from a minimum of three images acquired at different, but arbitrarily spaced, echo times. If the field heterogeneity map, $\psi$, is known, a minimum of two images acquired at different echo times are sufficient to estimate water and fat images.

The method of imaging different chemical species, such as water and fat, can be implemented with a single coil or with multiple coils. A field map of Bo heterogeneity is first calculated for each coil, and then the field maps are combined by weighting the contributions from each coil, such as by the square of the magnitude of the image contributed from each coil. Using the combined field map, images from each of the coils are recalculated, and the recalculated images are then combined, such as by taking the square root of the sum of the squares of the individual coil image signals. The combined field map can be smoothed by low pass filtering before the images are recalculated in order to improve noise performance.

The invention and objects and features thereof will be more readily apparent from the following detailed description and appended claims when taken with the drawings.

BRIEF DESCRIPTION OF THE DRAWINGS

FIGS. 2A-2D are images of knees constructed using the invention and using spoiled gradient echo (SPGR) imaging for comparison at 1.5 T.

Figures 4A, 4B, 4C:
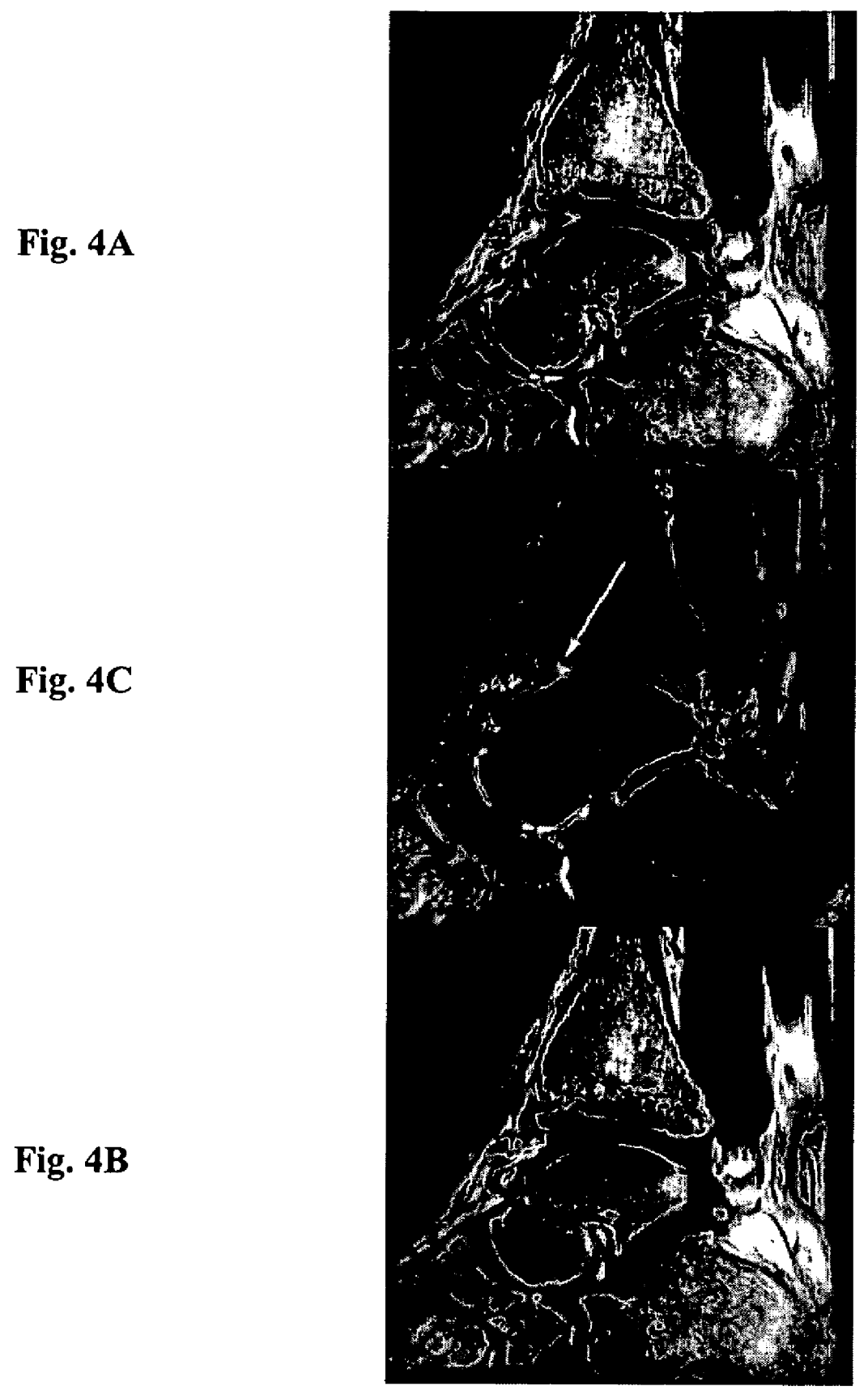

FIGS. 4A-4C are images of ankles constructed using the invention at 1.5 T.

FIGS. 5A-5D are images of knees constructed using the invention and using spoiled echo (SPGR) for comparison.

DETAILED DESCRIPTION OF ILLUSTRATED EMBODIMENTS

Figure 1A:
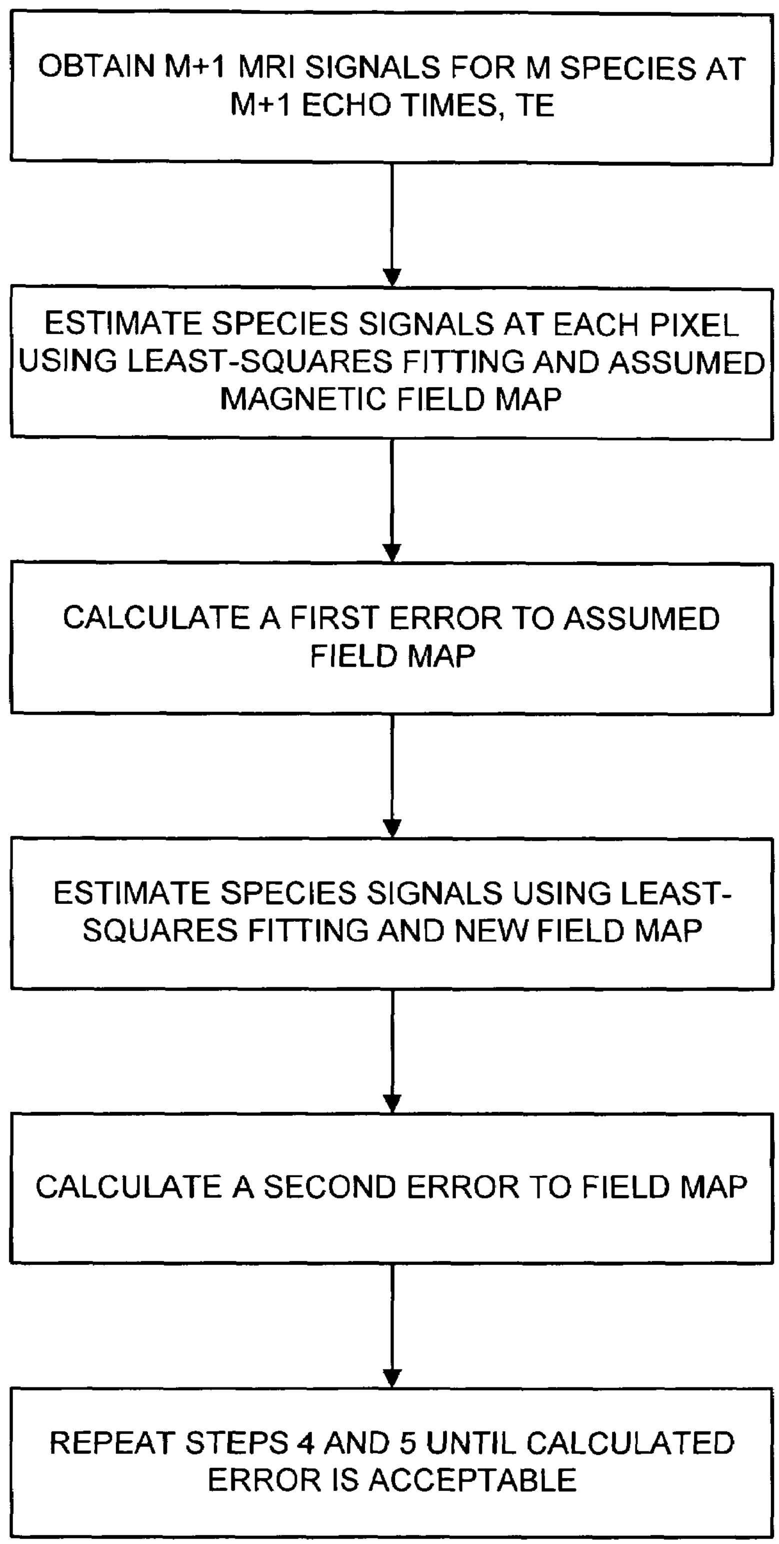
FIG. 1A is a flow diagram illustrating a magnetic resonance imaging using a single coil in accordance with one embodiment of the invention.
Figure 1B:
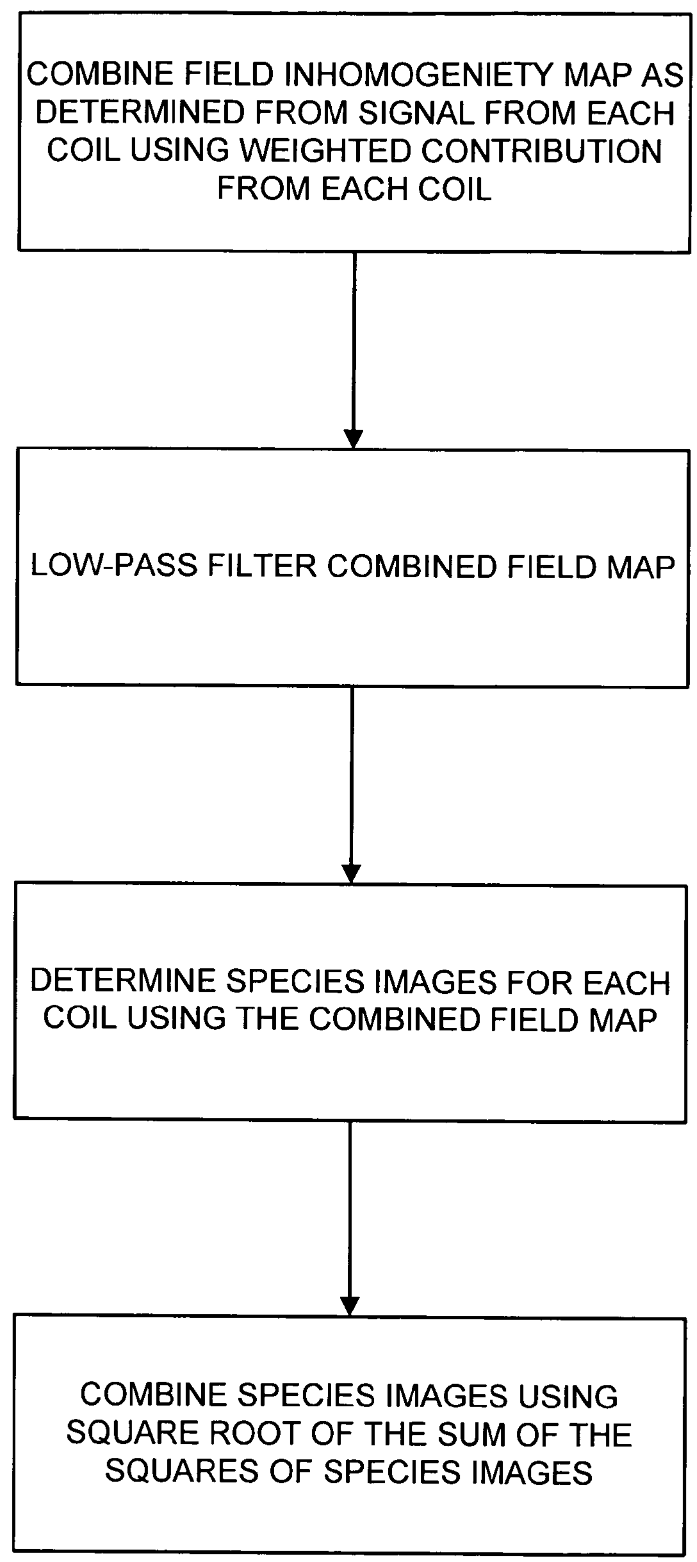
FIG. 1B is a flow diagram of another method of magnetic resonance imaging using a plurality of coils in accordance with another embodiment of the invention.
Figures 3A, 3B, 3C:
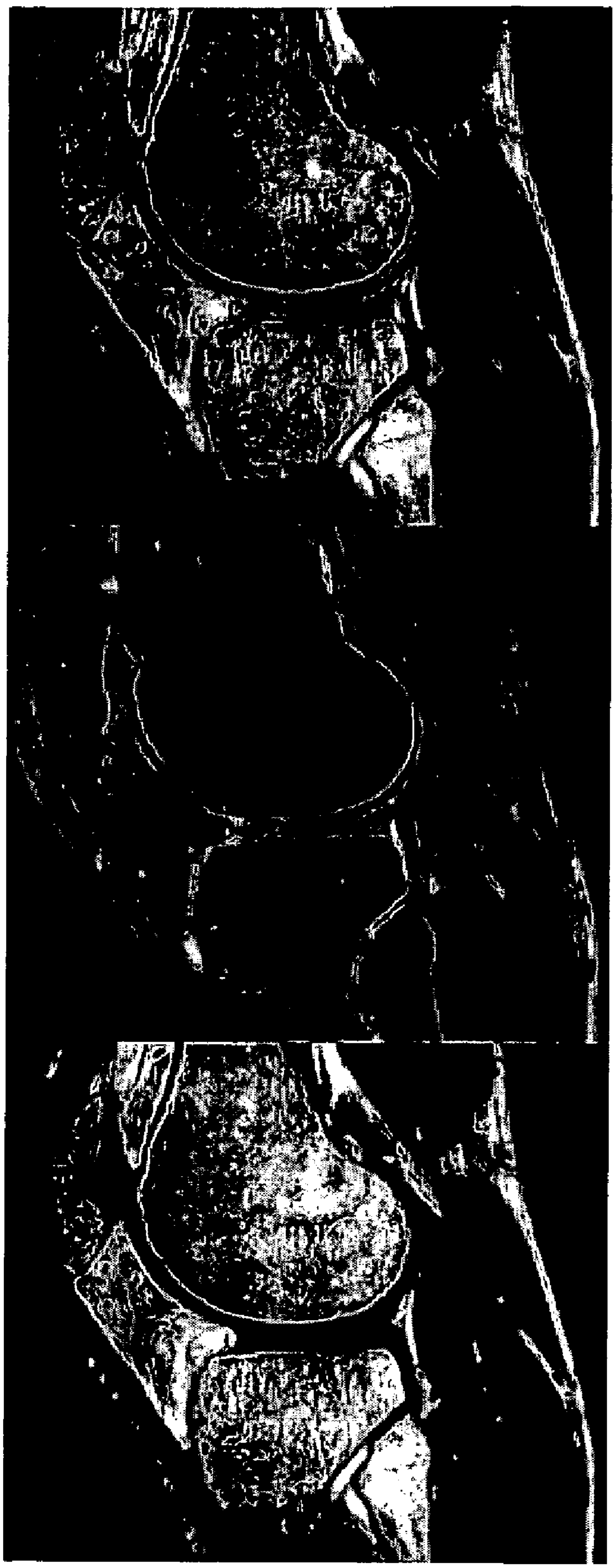
FIGS. 3A-3C are images of knees constructed using the invention at 3.0 T.

The present invention provides a new method for implementing fat-water separation utilizing a novel iterative least-squares method that reconstructs data acquired at short echo time increments, yielding images with high SNR and uniform separation of fat signal from water signal. The algorithm summarized in FIG. 1 extends naturally to multi-coil reconstruction with minimal additional complexity as summarized in FIG. 2. Single and multi-coil decompositions derived from images obtained at both 1.5 T and 3.0 T are shown. Examples in the knee, ankle, pelvis and heart are shown. An analysis of the noise performance of this method is provided and methods for improving noise performance through field map smoothing are discussed.

As noted above, the use of short echo times is necessary with SSFP to maintain short TR, thereby preventing image degradation from field heterogeneities. Three point methods described previously by Glover describe the special case of phase shifts of 0, π, and 2π which correspond to echo time increments of 0, 2.2 ms and 4.4 ms at 1.5 T and 0, 1.1 ms and 2.2 ms at 3.0 T. Unfortunately, such echo time increments cause significant lengthening TR. When using SSFP, increases in TR can lead to severe image degradation from banding artifacts caused by off-resonance field heterogeneities and chemical shift. Decomposition of water and fat using "Dixon" approaches requires shorter increments in echo time.

In accordance with the invention, an iterative linear least-squares approach is formulated and a generalized algorithm with arbitrary echo times and multiple chemical species is described below. The invention is extended to multi-coil applications, and an algorithm applies the invention to decomposition of each chemical species.

Consider the signal in an image from a pixel containing M species each with chemical shift $\Delta f_i$(Hz) located at position r, at an echo time t, $$s(r,t)=\left(\sum_{j=1}^{M}\rho_j e^{i2\pi\Delta f_j t}\right)e^{i2\pi\psi(r)t} \tag{1}$$

where $\rho_j$ is the signal from the $j^{th}$ species and is, in general, a complex term with its own magnitude, $|\rho_j|$ and phase, $\phi_j$, and $\psi(r)$ is the local magnetic field heterogeneity (Hz). If measurements are made at discrete echo times $t_n$(n=1, . . . , N), then, $$s_n(r)=\left(\sum_{j=1}^{M}\rho_j e^{i2\pi\Delta f_j t_n}\right)e^{i2\pi\psi(r)t_n} \tag{2}$$

representing the signal in a pixel located at position r at echo time $t_n$. Equation (2) contains M complex unknowns ($\rho_j$ (j=1, . . . M)) and one scalar unknown ($\psi$), for a total of 2M+1 unknowns. Each image contains a real and imaginary component, constituting two measurements per time point $t_n$. In general, M+1 or more images are required to determine the system and separate each chemical species. For example, with fat and water only (M=2), at least three or more images are required to decompose fat from water. If the relative phase between all $\rho_j$ were known, then only M images (=2 for fat and water, only) would be required for decomposition.

If an initial estimate of the field map $\psi_o(r)$ is known, then equation (2) can be rewritten, $$\hat{s}_n=s_n e^{-i2\pi\psi_o(r)t_n}=\sum_{j=1}^{M}\rho_j e^{i2\pi\Delta f_j t_n} \tag{3}$$

and is a linear system of complex equations that can be split into real ($\hat{s}_n^R$) and imaginary ($\hat{s}_n^I$) parts, $$\hat{s}_n=\hat{s}_n^R+i\hat{s}_n^I=\sum_{j=1}^{M}(\rho_j^R c_{jn}-\rho_j^I d_{jn})+i\sum_{j=1}^{M}(\rho_j^R d_{jn}+\rho_j^I c_{jn}) \tag{4}$$

where $\rho_j^R$ and $\rho_j^I$ are the real and imaginary components of the $j^{th}$ species, $C_{jn}=\cos(2\pi\Delta f_j t_n)$ and $d_{jn}=\sin(2\pi\Delta f_j t_n)$. Equation (4) forms a set of linear equations that is amenable to linear least squares fitting to decompose each chemical species. For n=1, . . . , N, equation (4) can be written in matrix format, $$\hat{S}=A\rho \tag{5}$$

where $\hat{S}=[\hat{s}_1^R\ \hat{s}_2^R\ \ldots\ \hat{s}_N^R \hat{s}_1^I\ \hat{s}_2^I\ \ldots\ \hat{s}_N^I]^T$, $\rho=[\rho_1^R\ \rho_1^I\ \rho_2^R\ \rho_2^I\ \ldots\ \rho_M^R\ \rho_M^I]^T$, and matrix A is provided below for M species:

$$A=\begin{bmatrix} c_{11} & -d_{11} & c_{21} & -d_{21} & \cdots & c_{M1} & -d_{M1} \\ c_{12} & -d_{12} & c_{22} & -d_{22} & \cdots & c_{M2} & -d_{M2} \\ \cdots & \cdots & \cdots & \cdots & \cdots & \cdots & \cdots \\ c_{1N} & -d_{1N} & c_{2N} & -d_{2N} & \cdots & c_{MN} & -d_{MN} \\ d_{11} & c_{11} & d_{21} & c_{21} & \cdots & d_{M1} & c_{M1} \\ d_{12} & c_{12} & d_{22} & c_{22} & \cdots & d_{M2} & c_{M2} \\ \cdots & \cdots & \cdots & \cdots & \cdots & \cdots & \cdots \\ d_{1N} & c_{1N} & d_{2N} & c_{2N} & \cdots & d_{MN} & c_{MN} \end{bmatrix} \tag{A.1}$$

where the rows 1 to N are used to calculate the real components of the signal, and rows N+1 to 2N are used to calculate the imaginary components of the signal.

Using well-described least squares fitting approaches for linear systems of equations, it can be shown that the least-squares estimate of ρ is, $$\hat{\rho}=(A^TA)^{-1}A^T\hat{S} \tag{6}$$

From equation (6), initial estimates of the water and fat images can be determined from $\hat{\rho}=[\hat{\rho}_1^R\ \hat{\rho}_1^I\ \hat{\rho}_2^R\ \hat{\rho}_2^I\ \ldots\ \hat{\rho}_M^R\ \hat{\rho}_M^I]^T$.

The initial estimate of the field map ($\psi_o$) is further refined by defining error terms: $\psi=\psi_o+\Delta\psi$, $\rho_j^R=\hat{\rho}_j^R+\Delta\rho_j^R$, and $\rho_j^I=\hat{\rho}_j^I+\Delta\rho_j^I$. Inserting these expressions into equation (2) it is shown in the appendix that for small $\Delta\psi$, $\Delta\rho_j^R$ and $\Delta\rho_j^I$, that, $$\hat{S}\approx By \tag{7}$$

where $y=[\Delta\psi\ \Delta\rho_1^R\ \Delta\rho_1^I\ \Delta\rho_2^R\ \Delta_2^I \ldots \Delta\rho_M^R\ \Delta\rho_M^I]^T$, and $\hat{S}$ and B are both defined in the appendix. For n=1, . . . , N, equation (7) is a linear system of equations, and similar to above, estimates of y can be calculated as, $$y=(B^T B)^{-1} B^T \hat{S} \quad (8).$$

In the special case of a system with only water and fat ($\Delta f_{fw}$ chemical shift) and the receive/transmit frequency of the scanner is set to water, matrices A and B become, $$A = \begin{bmatrix} 1 & 0 & c_1^{fw} & -d_1^{fw} \\ 1 & 0 & c_2^{fw} & -d_2^{fw} \\ \ldots & \ldots & \ldots & \ldots \\ 1 & 0 & c_N^{fw} & -d_N^{fw} \\ 0 & 1 & d_1^{fw} & c_1^{fw} \\ 0 & 1 & d_2^{fw} & c_2^{fw} \\ \ldots & \ldots & \ldots & \ldots \\ 0 & 1 & d_N^{fw} & c_N^{fw} \end{bmatrix} \text{ and } B = \begin{bmatrix} g_1^R & 1 & 0 & c_1^{fw} & -d_1^{fw} \\ g_2^R & 1 & 0 & c_2^{fw} & -d_2^{fw} \\ \ldots & \ldots & \ldots & \ldots & \ldots \\ g_N^R & 1 & 0 & c_N^{fw} & -d_N^{fw} \\ g_1^I & 0 & 1 & d_1^{fw} & c_1^{fw} \\ g_2^I & 0 & 1 & d_2^{fw} & c_2^{fw} \\ \ldots & \ldots & \ldots & \ldots & \ldots \\ g_N^I & 0 & 1 & d_N^{fw} & c_N^{fw} \end{bmatrix}$$

where $c_n^{fw}=\cos(2\pi\Delta f_{fw} t_n)$, $d_n^{fw}=\sin(2\pi\Delta f_{fw} t_n)$, $g_n^R=2\pi t_n(-\hat{\rho}_w^I-\hat{\rho}_f^R d_n-\hat{\rho}_f^I c_n)$ and $g_n^I=2\pi t_n(\hat{\rho}_w^R+\hat{\rho}_f^R c_n-\rho_f^I d_n)$ are the matrix elements.

Using the above equations, the following algorithm summarizes the method used to determine the least-squares estimates of different chemical species, such as water images, fat images, and silicone images for each pixel using a single coil acquisition:

a) estimate water and fat assuming with equation (6), and initial guess for field map, $\psi_o$, A useful initial guess is zero (Hz);
b) calculate error to field map, $\Delta\psi$ using equation (8);
c) recalculate $\psi=\psi_o+\Delta\psi$;
d) recalculate $\hat{S}=[\hat{s}_1\ \hat{s}_2 \ldots \hat{s}_N]^T$ with the new estimate of $\psi$ using equation (6);
e) repeat steps b) through d) until $\Delta\psi$ is small (e.g., <1 Hz).

A multi-coil acquisition with P elements collects P independent images, all with a different relative phase offset. By using the above algorithm, P separate water and fat images can be generated, as well as P field heterogeneity maps. The field maps can then be combined by weighting the contribution from each coil by the square of the magnitude of the image contributed by that coil. Specifically, for each pixel at position r, the combined field map can be calculated as, $$\psi_c(r) = \frac{\sum_{p=1}^{P} \psi_p(r)|s_p|^2}{\sum_{p=1}^{P} |s_p|^2}. \quad (11)$$

Using the combined field map, $\hat{S}=Se^{-i2\pi\psi_c(r)}$ is then recalculated and estimates of the water and fat images are calculated for each coil from equation (6). Finally, the M water and fat images are combined using the square root of the sum of the square, a commonly used multi-coil reconstruction.

A summary of the final fat-water decomposition is provided below, taking into account the use of multi-coil acquisitions, as well as smoothing of the final field map:

For each coil:
for each pixel;
a) estimate water and fat assuming initial guess for field map, $\psi_o$, from equation (6);
b) calculate error to field map, $\Delta\psi$, from equation (8);
c) recalculate $\psi=\psi_o+\Delta\psi$;
d) recalculate $\hat{S}=[\hat{s}\ \hat{s} \ldots \hat{s}_N]^T$ with the new estimate of $\psi$; and
e) repeat steps b) through d) until $\Delta\psi$ is small.

For multi-coil acquisitions, combine field map with equation (11).

Smooth field map with low-pass filter.

Recalculate final estimate of each water and fat image with equation (6) using the filtered combined field map.

Multi-coil combination of water (fat) images using the square root of the sum of the squares for all signals.

A three dimensional (3-D) SSFP imaging sequence was used on a 1.5 T and a 3.0 T GE Signa scanner to acquire source, calculated water and calculated fat images from knees (FIGS. 2A-2D, FIGS. 3A-3C), ankles (FIGS. 4A-4C, FIGS. 5A-5D) and abdomens (FIG. 6) from normal volunteers.

A product extremity coil was used for the knees and ankles and the body coil was used for abdominal imaging. Pulse sequence parameters included: BW=125 kHz, $N_x$=256, $N_y$=192, NSA=1. For the knee and ankle: FOV=16 cm, slice=1.5 mm, $N_z$=64, TR=6.2, TE=(2.02, 2.69, 3.35, 4.02 ms), total scan time of 5:02 min. Pelvis: FOV=32 cm, slice=5 mm, $N_z$=22, TR=5.4 ms, TE=(1.58, 2.24, 2.91, 3.58 ms), total scan time of 1:30 min.

For comparison, 3D spoiled gradient echo (SPGR) images with fat saturation were obtained in the knees and ankles (FIGS. 2D, 5D). Matrix size, field of view and slice thickness were all the same. Other parameters included: TR=50 ms, TE=5 ms (full echo), tip angle=40°, and BW=±16 kHz. These parameters are based on established reports using fat saturated SPGR imaging of articular cartilage.

Figure 6A:
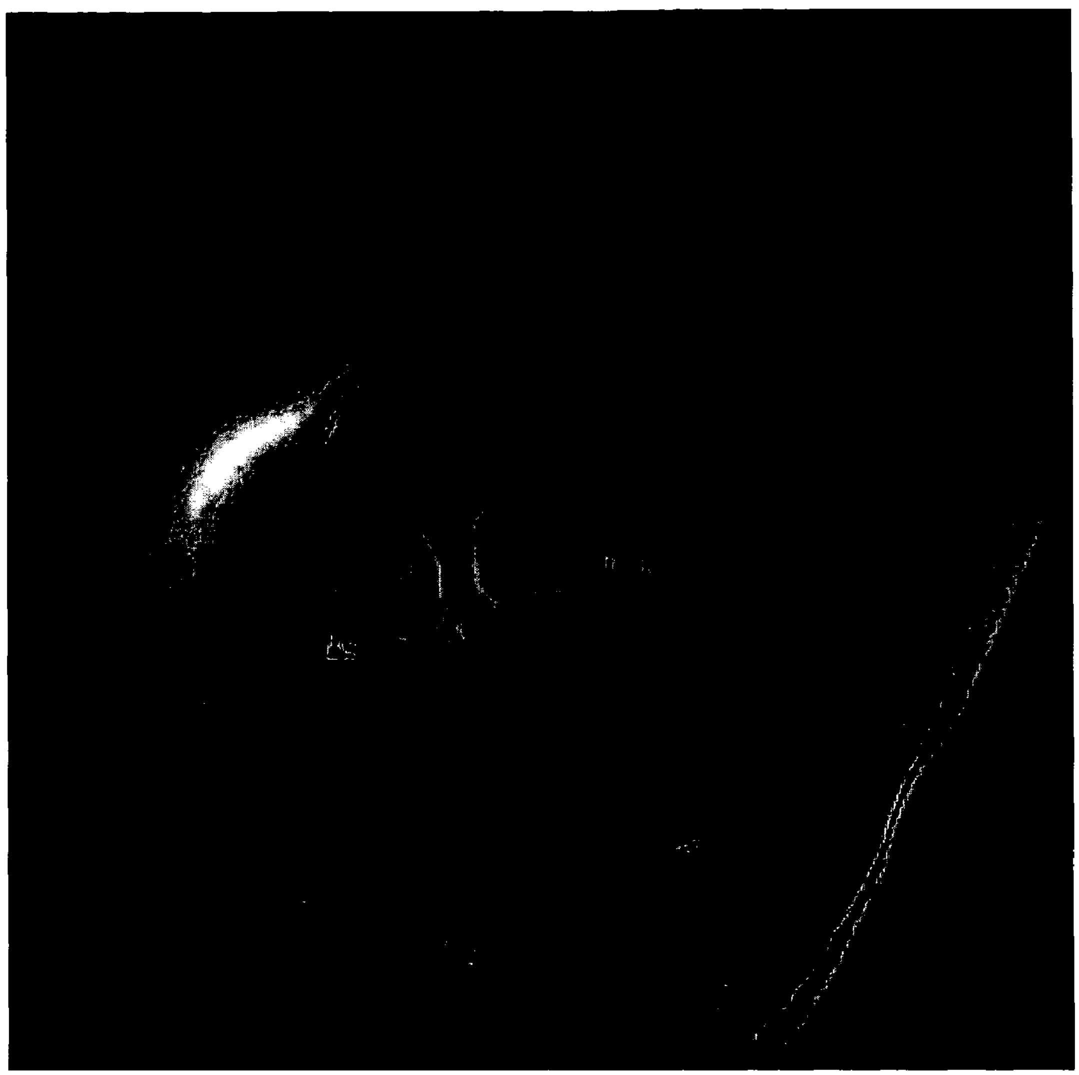
FIG. 6 is cardiac images using the invention and acquired throughout the cardiac cycle including source images and calculated water and fat images using the invention.
Figure 6B:
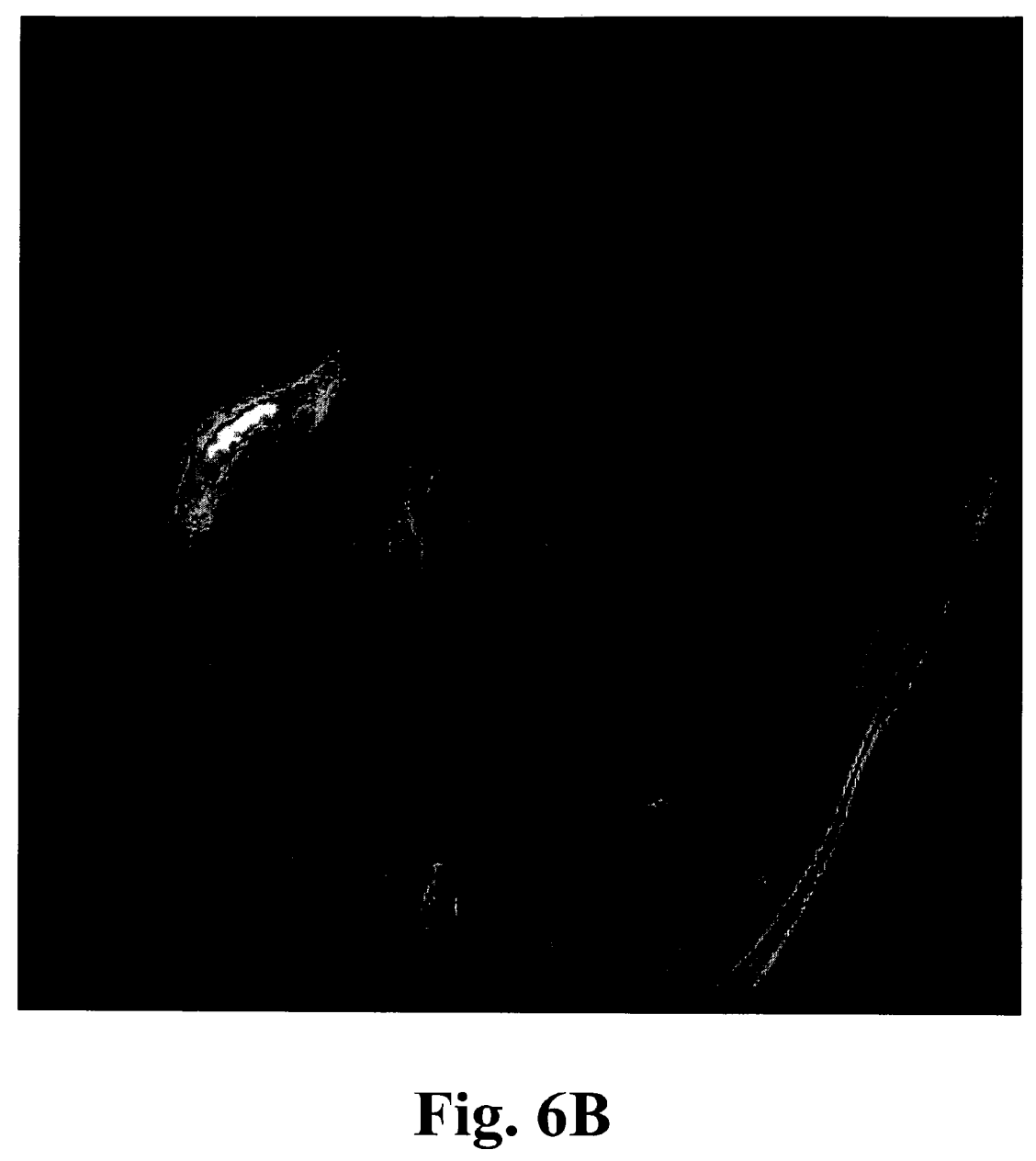
Figure 6C:
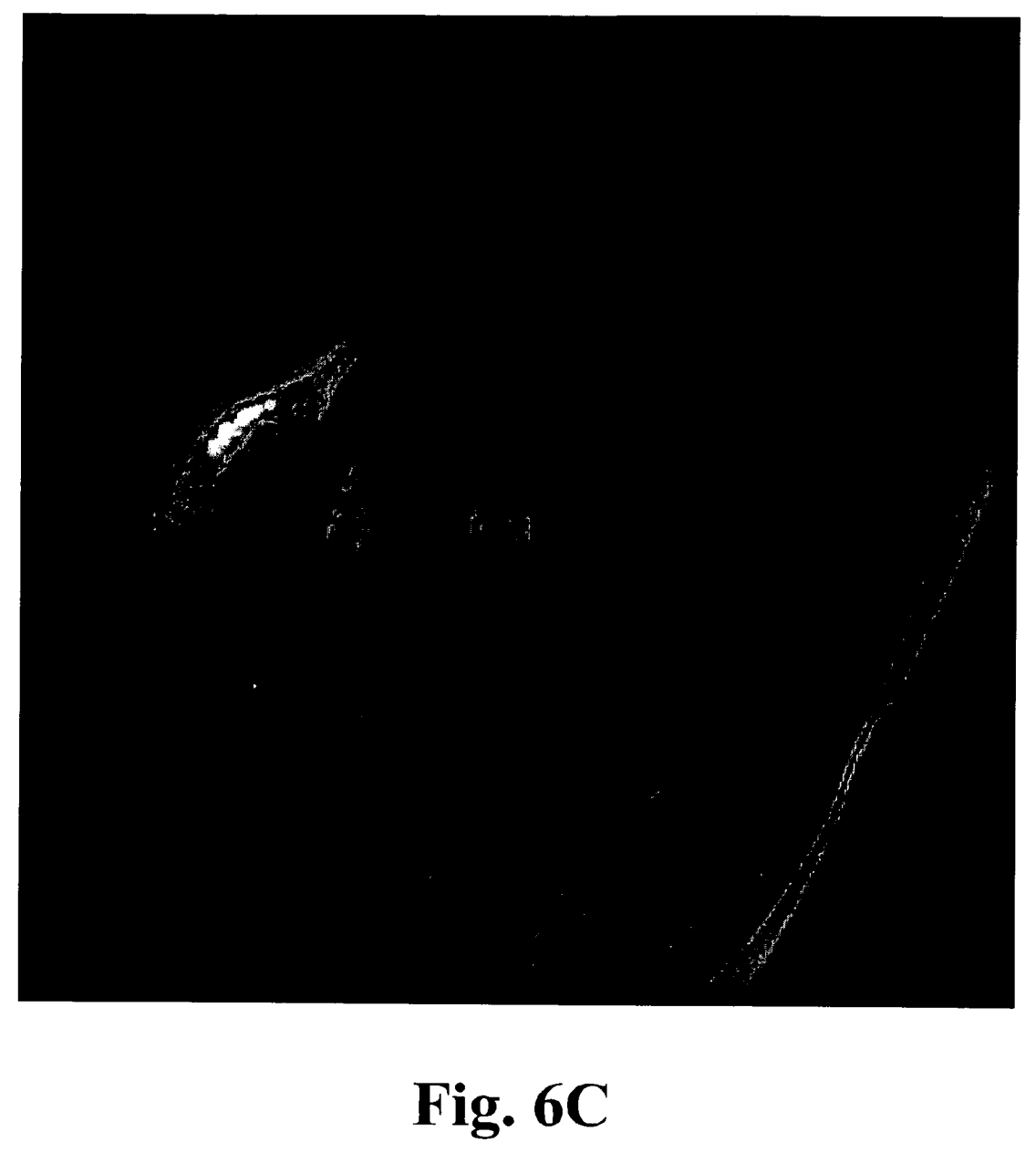
Figure 6D:
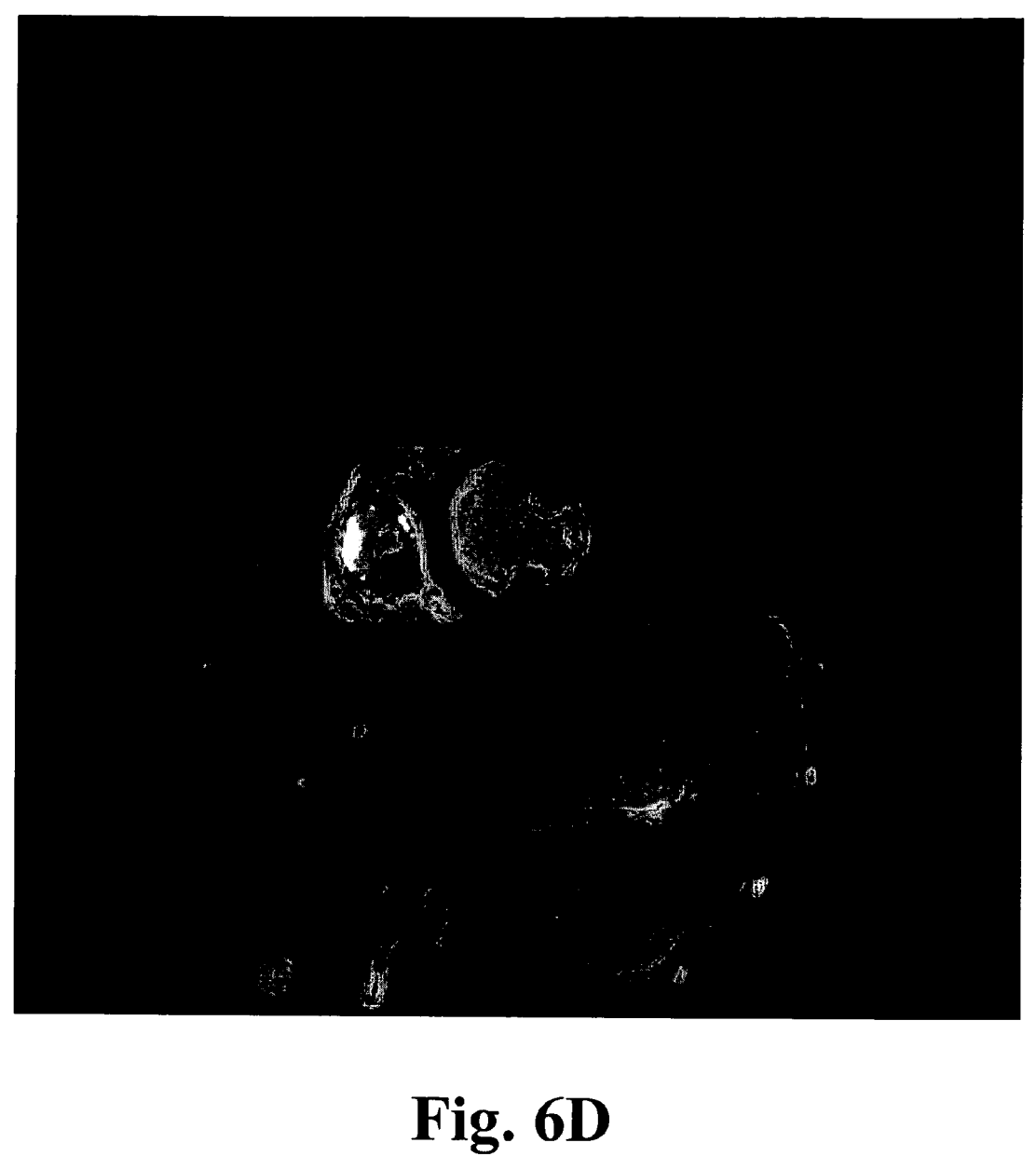
Figure 6E:
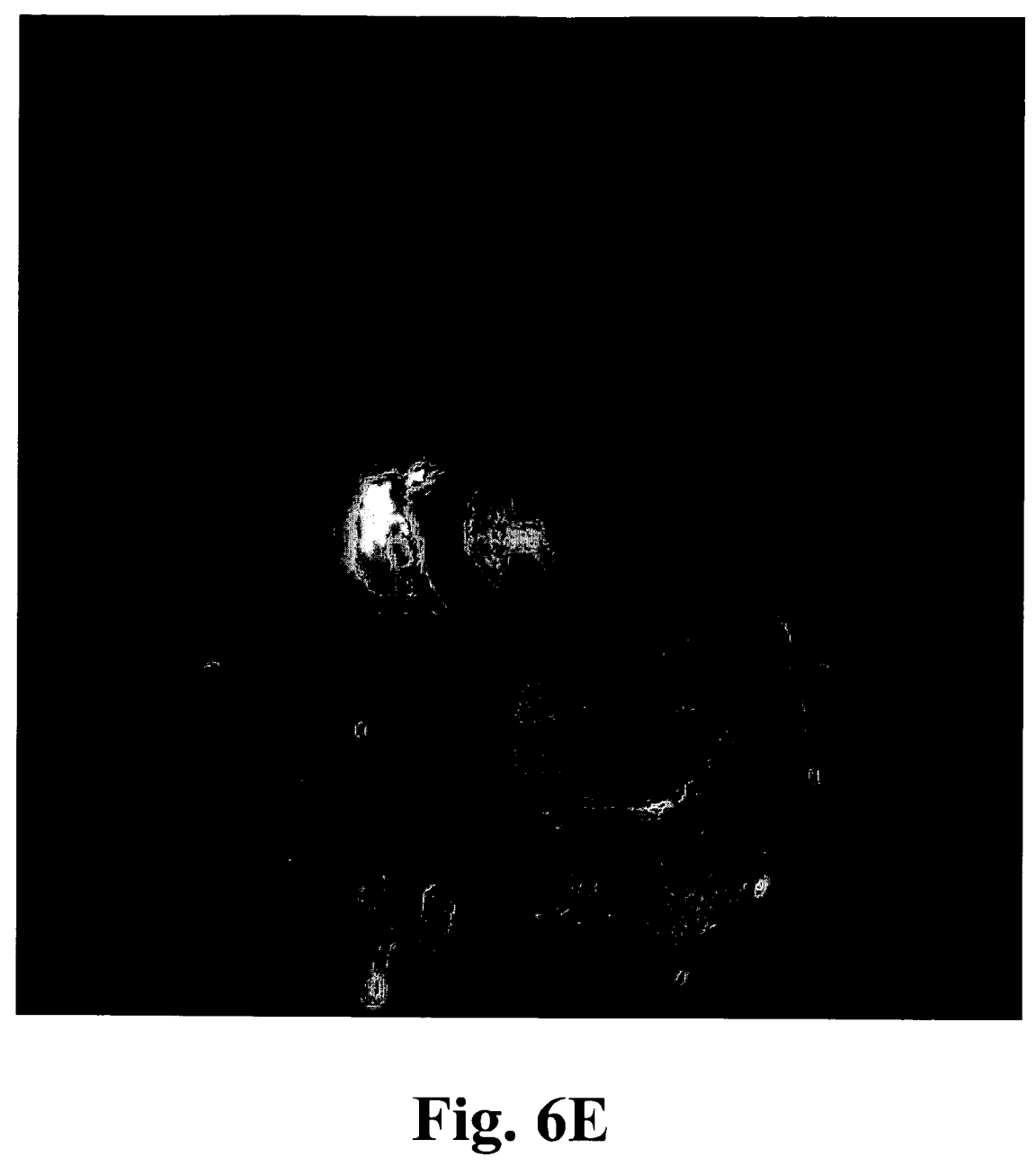
Figure 6G:
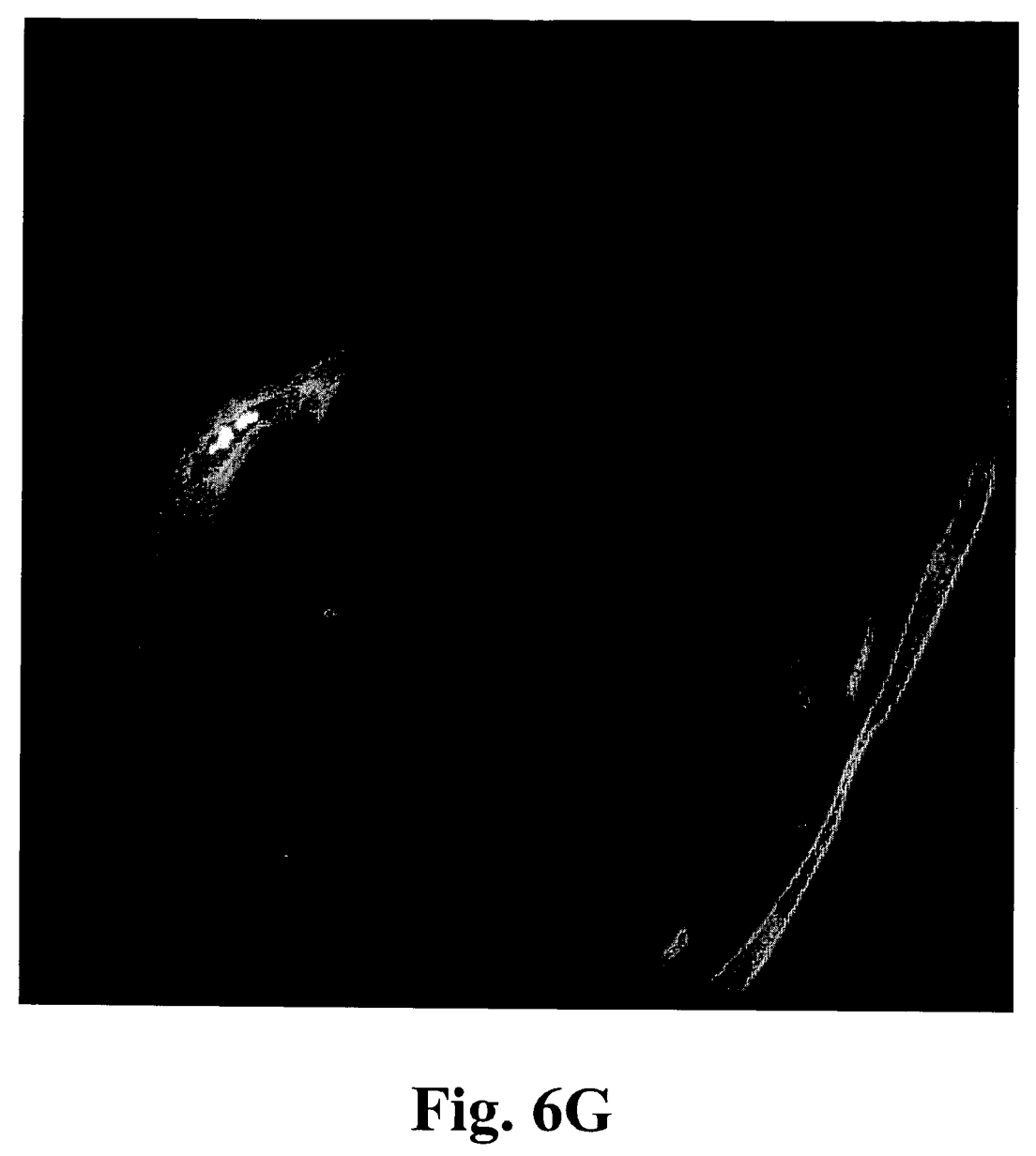
Figure 6H:
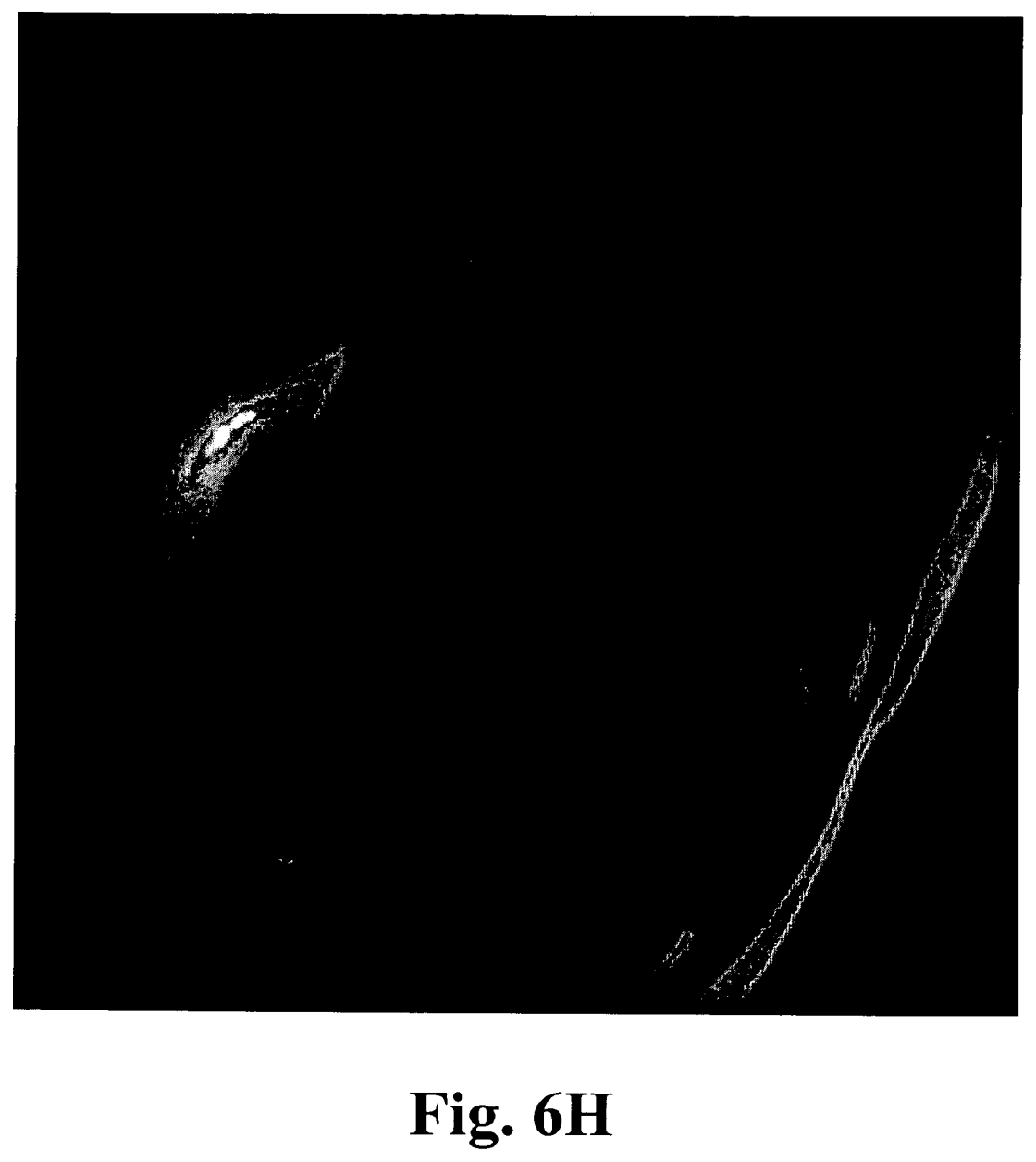
Figure 6I:
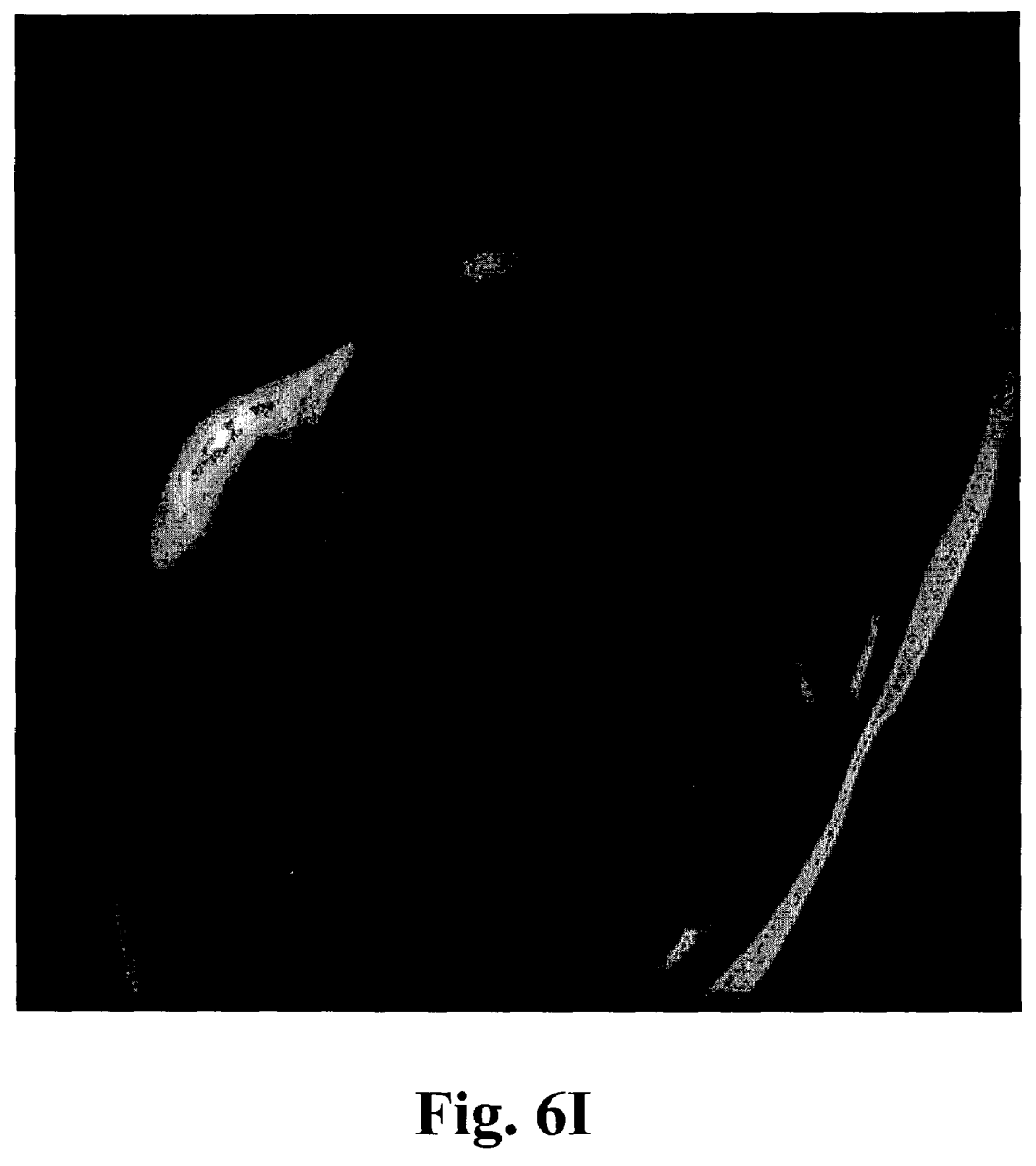

FIGS. 6A-6I are retrospectively ECG gated cardiac CINE SSFP images acquired at end-diastole, mid-systolic, and end-systolic, respectively, for source images (FIGS. 6A-6C), calculated water images (FIGS. 6D-6F), and calculated fat images (FIGS. 6G-6I).

An off-line reconstruction program written in Matlab 6.0 (Mathworks, Mountain View, Calif.) was used to perform fast Fourier transform reconstruction of all images. Following reconstruction of complex (magnitude and phase) images, estimation of water images and fat images based on the iterative least-squares algorithm was performed.

Multi-point techniques have been combined with short TR and TE sequences such as SSFP to obtain excellent fat-water separation, using iterative least-squares fitting approaches that allow the use of short echo time increments. This invention is particularly attractive because it does not require evenly-spaced echo time increments. In addition, phase-unwrapping algorithms are not necessary. While the invention works well with short TE/short TR sequences, the method works with other sequences in "Dixon" imaging.

Incorporated herein by reference for all purposes and attached hereto as Appendix B is a copy of a paper submitted to Magnetic Resonance in Medicine which has been accepted for publication. The paper is entitled "Multi-coil "Dixon" Chemical Species Separation with an Iterative Least Squares Estimation Method", by Scott B. Reeder, Zhifei Wen, Huanzhou Yu, Angel R. Pineda, Garry E. Gold, Michael Markl, and Norbert J. Pelc.

While the invention has been described with reference to specific embodiments, the description is illustrative of the invention and is not to be construed as limiting the invention. For example, rather than filtering the combined field map, the source images can be smoothed by filtering before calculating the field map. Then with this field map, go back to the original unfilitered source images and calculate the water and fat images. Thus, various modifcations and applications may occur to those skilled in the art without departing from the true scope and spirit of the invention as defined by the appended claims.

What is claimed is:

1. A method of obtaining magnetic resonance signals with signal separation for at least two chemical species in a heterogeneous magnetic field using rapid gradient echo imaging, comprising the steps of:

a) obtaining first magnetic resonance signals from pixels in an object having at least two chemical species using a first repetition time and a first echo time, b) obtaining at least second and third magnetic resonant signals from the pixels using second and third echo times, wherein the magnetic resonance signals at time, n=1 to N, for species, j =1 to M, having real, R, and imaginary, I, parts is given by:

$$\hat{s}_n = \hat{s}_n^R + i\hat{s}_n^I = \sum_{j=1}^{M}(\rho_j^R c_{jn} - \rho_j^I d_{jn}) + i\sum_{j=1}^{M}(\rho_j^R d_{jn} + \rho_j^I c_{jn})$$

and a least squares fitting of all signals is given by:

$$\hat{\rho}=(A^TA)^{-1}A^T\hat{S}$$

where A is a known matrix for M species, c) determining a signal estimate for each species and for each pixel by combining all measured signals for the pixel using a linear least squares fitting directly on the signals from each pixel to decompose the chemical species, assuming a first value of field heterogeneity ($\psi_0$), d) calculating a first error to the field heterogeneity, e) repeating step c) using the first value of field heterogeneity and the error from step d), f) repeating step d) to calculate a second error to the field heterogeneity, and g) updating the value of field heterogeneity and repeating steps c) and d) until an acceptable error is calculated, wherein:

$$A = \begin{bmatrix} c_{11} & -d_{11} & c_{21} & -d_{21} & \cdots & c_{M1} & -d_{M1} \\ c_{12} & -d_{12} & c_{22} & -d_{22} & \cdots & c_{M2} & -d_{M2} \\ \cdots & \cdots & \cdots & \cdots & \cdots & \cdots & \cdots \\ c_{1N} & -d_{1N} & c_{2N} & -d_{2N} & \cdots & c_{MN} & -d_{MN} \\ d_{11} & c_{11} & d_{21} & c_{21} & \cdots & d_{M1} & c_{M1} \\ d_{12} & c_{12} & d_{22} & c_{22} & \cdots & d_{M2} & c_{M2} \\ \cdots & \cdots & \cdots & \cdots & \cdots & \cdots & \cdots \\ d_{1N} & c_{1N} & d_{2N} & c_{2N} & \cdots & d_{MN} & c_{MN} \end{bmatrix}$$

where $c_n^{fw}=\cos(2\pi\Delta f_{fw}t_n)$, $d_n^{fw}=\sin(2\pi\Delta f_{fw}t_n)$, $g_n^R=2\pi t_n(-\hat{\rho}_w^I-\hat{\rho}_f^R d_n-\hat{\rho}_f^I c_n)$ and $g_n^I=2\pi t_n(\hat{\rho}_w^R+\hat{\rho}_f^R c_n-\rho_f^I d_n)$ are the matrix elements.

2. A method of obtaining magnetic resonance signals with signal separation for at least two chemical species in a heterogeneous magnetic field using rapid gradient echo imaging, comprising the steps of:

a) obtaining first magnetic resonance signals from pixels in an object having at least two chemical species using a first repetition time and a first echo time, b) obtaining at least second and third magnetic resonant signals from the pixels using second and third echo times, wherein the magnetic resonance signals at time, n=1 to N, for species, j=1 to M, having real, R, and imaginary, I, parts is given by:

$$\hat{s}_n = \hat{s}_n^R + i\hat{s}_n^I = \sum_{j=1}^{M}(\rho_j^R c_{jn} - \rho_j^I d_{jn}) + i\sum_{j=1}^{M}(\rho_j^R d_{jn} + \rho_j^I c_{jn})$$

and a least squares fitting of all signals is given by:

$$\hat{\rho}=(A^TA)^{-1}A^T\hat{S}$$

where A is a known matrix for M species, c) determining a signal estimate for each species and for each pixel by combining all measured signals for the pixel using a linear least squares fitting directly on the signals from each pixel to decompose the chemical species, assuming a first value of field heterogeneity ($\psi_o$), d) calculating a first error to the field heterogeneity, wherein error to the field heterogeneity is given by:

$$y=(B^TB)^{-1}B^T\hat{S}$$

where B is a matrix given by:

$$B = \begin{bmatrix} g_{11}^R & c_{11} & -d_{11} & c_{21} & -d_{21} & \cdots & c_{M1} & -d_{M1} \\ g_{12}^R & c_{12} & -d_{12} & c_{22} & -d_{22} & \cdots & c_{M2} & -d_{M2} \\ \cdots & \cdots & \cdots & \cdots & \cdots & \cdots & \cdots & \cdots \\ g_{1N}^R & c_{1N} & -d_{1N} & c_{2N} & -d_{2N} & \cdots & c_{MN} & -d_{MN} \\ g_{11}^I & d_{11} & c_{11} & d_{21} & c_{21} & \cdots & d_{M1} & c_{M1} \\ g_{12}^I & d_{12} & c_{12} & d_{22} & c_{22} & \cdots & d_{M2} & c_{M2} \\ \cdots & \cdots & \cdots & \cdots & \cdots & \cdots & \cdots & \cdots \\ g_{1N}^I & d_{1N} & c_{1N} & d_{2N} & c_{2N} & \cdots & d_{MN} & c_{MN} \end{bmatrix}$$

where $$y = [\,\Delta\psi \;\; \Delta\rho_1^R \;\; \Delta\rho_1^I \;\; \Delta\rho_2^R \;\; \Delta\rho_2^I \;\; \cdots \;\; \Delta\rho_M^R \;\; \Delta\rho_M^I\,]^T,$$

$$g_{jn}^R = 2\pi t_n\sum_{j=1}^{M}(-\hat{\rho}_j^R d_{jn} - \hat{\rho}_j^I c_{jn}) \text{ and}$$

$$g_{jn}^I = 2\pi t_n\sum_{j=1}^{M}(\hat{\rho}_j^R c_{jn} - \hat{\rho}_j^I d_{jn}).$$

e) repeating step c) using the first value of field heterogeneity and the error from step d), f) repeating step d) to calculate a second error to the field heterogeneity, and g) updating the value of field heterogeneity and repeating steps c) and d) until an acceptable error is calculated.

3. The method as defined by claim 2 wherein M chemical species are present and step b) includes obtaining at least M+1 magnetic resonance signals for each pixel.

4. The method as defined by claim 2 wherein fat and water are two chemical species and step b) includes obtaining three magnetic resonance signals.

5. The method as defined by claim 2 wherein step a) includes obtaining signals from a single coil.

6. The method as defined by claim 2 wherein step a) includes obtaining signals from a plurality of coils and steps b) through g) are performed for signals from each coil, and further including the step of:

h) combining field heterogeneity as determined from signals for each coil.

7. The method as defined by claim 6 wherein field heterogeneity is determined by weighting contributions from each coil.

8. The method as defined by claim 7 wherein the weighting contribution from each coil is a function of the square of the magnitude of the image contributed by that coil.

9. The method as defined by claim 8 where for each pixel, at position r, the combined field map is:

$$\psi_c(r) = \frac{\sum_{p=1}^{P} \psi_p(r)|s_p|^2}{\sum_{p=1}^{P} |s_p|^2}$$

where P coils collect P independent images.

10. The method as defined by claim 9 wherein the combined field heterogeneity from step h) is smoothed by passing through a low pass filter.

11. The method as defined by claim 9 wherein M images of each species are obtained using signals from each of M coils and the combined field heterogeneity, and then combining the M images using a square root of the sum of the squares of the images.

12. The method as defined by claim 2 wherein step a) includes obtaining signals from a plurality of coils and steps b) through g) are performed for signals from each coil, and further including the step of:

h) combining field heterogeneity as determined from signals for each coil.

13. The method as defined by claim 12 wherein field heterogeneity is determined by weighting contributions from each coil.

14. The method as defined by claim 13 wherein the weighting contribution from each coil is a function of the square of the magnitude of the image contributed by that coil.

15. The method as defined by claim 14 where for each pixel, at position r, the combined field map is:

$$\psi_c(r) = \frac{\sum_{p=1}^{P} \psi_p(r)|s_p|^2}{\sum_{p=1}^{P} |s_p|^2}$$

where P coils collect P independent images.

16. The method as defined by claim 15 wherein the combined field heterogeneity from step h) is smoothed by passing through a low pass filter.

17. The method as defined by claim 15 wherein M images of each species is obtained using signals from each of M coils and the combined field heterogeneity, and then combining the M images using a square root of the sum of the squares of the images.

* * * * *